United States Patent
Lam et al.

(10) Patent No.: US 11,241,375 B2
(45) Date of Patent: Feb. 8, 2022

(54) COSMETIC COMPOSITION COMPRISING BIODEGRADABLE POLYMERS

(71) Applicant: L'ORÉAL, Paris (FR)

(72) Inventors: Hubert Tunchiao Lam, New Providence, NJ (US); Christopher Pang, New York, NY (US)

(73) Assignee: L'ORÉAL, Paris (FR)

( * ) Notice: Subject to any disclaimer, the term of this patent is extended or adjusted under 35 U.S.C. 154(b) by 30 days.

(21) Appl. No.: 16/587,357

(22) Filed: Sep. 30, 2019

(65) Prior Publication Data
US 2021/0093546 A1    Apr. 1, 2021

(51) Int. Cl.
| | | |
|---|---|---|
| A61K 8/85 | (2006.01) |
| A61K 8/92 | (2006.01) |
| A61Q 1/10 | (2006.01) |
| C08L 67/04 | (2006.01) |

(52) U.S. Cl.
CPC .............. *A61K 8/85* (2013.01); *A61K 8/92* (2013.01); *A61Q 1/10* (2013.01); *C08L 67/04* (2013.01); *A61K 2800/42* (2013.01)

(58) Field of Classification Search
None
See application file for complete search history.

(56) References Cited

U.S. PATENT DOCUMENTS

| | | |
|---|---|---|
| 8,968,787 B2 | 3/2015 | Gittleman |
| 2010/0158832 A1* | 6/2010 | Chodorowski-Kimmes ............... A61Q 1/02 424/59 |
| 2014/0026916 A1 | 1/2014 | Havens et al. |
| 2020/0268637 A1* | 8/2020 | Czarnecki ............... A61Q 1/12 |

FOREIGN PATENT DOCUMENTS

| | | | |
|---|---|---|---|
| EP | 0681830 A1 | 11/1995 | |
| WO | 2010103215 A1 | 9/2010 | |
| WO | WO-2012035029 A2 * | 3/2012 | ............... A61K 8/19 |
| WO | 2014010098 A1 | 1/2014 | |

* cited by examiner

*Primary Examiner* — Michael B. Pallay
(74) *Attorney, Agent, or Firm* — Meagher Emanuel Laks; Goldberg & Liao, LLP

(57) ABSTRACT

Disclosed is a cosmetic composition for, e.g., use on eyelashes, that includes a latex polymer and a polyhydroxyalkanoate, where the polyhydroxyalkanoate is present in the composition in a total amount of between about 1% and about 5% by weight, and the monomers of the polyhydroxyalkanoate have carbon chain lengths of between 3 and 5.

17 Claims, No Drawings

COSMETIC COMPOSITION COMPRISING BIODEGRADABLE POLYMERS

FIELD OF THE INVENTION

The present invention relates to cosmetic compositions, and specifically to cosmetic composition utilizing a latex polymer or wax waterproofing agent and a polyhydroxyalkanoate, where the formula has less than about 10% water by weight.

BACKGROUND

Makeup products, especially mascaras, are expected to have good wear and transfer resistance properties. The cosmetics industry focuses much of its efforts, with regards to mascara, on increasing two fundamental properties, namely enhancing volume or thickness of eyelashes and extending length of wear. With regard to this expectation, currently marketed mascaras are typically comprised of an emulsion of water and waxes to provide volume, length, and other attributes. The challenge of continuing to improve the volume and length of wear is challenged by competing interests from consumers, such as the desire for designers to consider environmental impact of its product, and also for having cosmetics that are readily removable. Therefore, a cosmetic product with biodegradable polymers that has improved volume and removability is desirable.

BRIEF SUMMARY

A first aspect of the present disclosure is a cosmetic composition that includes a latex polymer or wax waterproofing agent and a polyhydroxyalkanoate (PHA). The PHA is present in the composition in a total amount of between about 0.5% and about 15% by weight (preferentially between 1-5%). The PHA should be provided in form of a powder, such as those comprised of monomers having carbon chain lengths of between 3 and 5. Powder in this case is referring to the physical state of the polymer in the powder form, which retains its shape and morphology in the cosmetic composition under normal conditions of use. Optionally, the polyhydroxyalkanoate is poly-3-hydroxybutyrate (PH3B) and/or poly(3-hydroxybutyrate-co-3-hydroxyvalerate) (PHBV) and/or a PHA copolymer made with 3 hydroxybutyric acid and hydroxypentanoic acid. Optionally, each polyhydroxyalkanoate in the composition is composed of only one monomer. In some embodiments, the composition does not include any polyhydroxyalkanoates with monomers having a carbon chain length greater than 5.

In some embodiments, the polyhydroxyalkanoate is a solid particle, and may have an average particle size (d50) between about 0.1 nm and 100 μm.

Optionally, the composition may include other ingredients, such as a colorant or a wax.

The cosmetic composition according to claim 1, wherein the composition does not include any cellulose or cellulose derivatives.

A second aspect of the present disclosure is a method for treating eyelashes. The method includes applying a disclosed cosmetic composition to an eyelash and allowing the cosmetic composition to remain in contact with the eyelash. Optionally, the cosmetic composition may remain on the eyelash for between 5 minutes and 24 hours. Optionally, the method includes removing the cosmetic composition via, e.g., wiping the composition off using a cosmetic cleanser).

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "between [two numbers]" is intended to include those two numbers. For example, "x is between 1 and 2" is intended to cover $1 \leq x \leq 2$.

As used herein, the terms "include", "includes" and "including" are meant to be non-limiting.

A first aspect of the present disclosure is a cosmetic composition that includes a latex polymer or wax waterproofing agent and a polyhydroxyalkanoate, wherein the composition comprises less than about 10% water by weight. In some embodiments, the composition comprises less than 5% water. In some embodiments, the composition contains less than 1% water.

Waterproofing Agent

As disclosed herein, the waterproofing agent(s) should be a latex polymer or a wax.

Latex Polymer

While any latex polymer known to those of skill in the art may be utilized, latex polymer may optionally be chosen from latex film forming polymers such as polyacrylate latex, polyurethane latex, and their copolymers.

Non-limiting examples of suitable latex polymers include ethylhexyl acrylate/hema copolymer (and) acrylates/diethylaminoethyl methacrylate/ethylhexyl acrylate copolymer (Syntran® PC 5775), styrene/acrylates/ammonium methacrylate copolymer (Syntran® 5760, Syntran® 5009, Syntran® PC5620), polyacrylate-21 (and) acrylates/dimethylaminoethyl methacrylate copolymer (Syntran® PC5100, Syntran® PC5776, Eudragit® E 100, Jurymer ET-410C), styrene/acrylates/ammonium methacrylate copolymer (Syntran® 5009 CG), olefin/acrylate grafted polymer (and) sodium laureth sulfate (and C12-15 SEC-pareth 15 (Syntran® EX108), acrylates copolymer (Aculyn® 33A Polymer, Avalure® Ace 210/120/315 Acrylic Copolymer, Carbopol® Aqua SF-1 Polymer, Daitosol® 500 AD, Coatex® Co 633, Eliclear® 380/700/4U, Eudragit® L 100, Joncryl® 85, Luviflex® Soft), acrylates/ethylhexyl acrylate copolymer (Daitosol® 5000SJ, Daitosol® 4000SJT, MJA PS34-21, SDP-001). The Syntran® polymers are commercially available from the supplier Interpolymer Corp.

Other optional latex polymers are polyurethane-35, polyurethane-35, and polyurethane-35. Non-limiting examples of suitable polyurethanes include, but are not limited to, products sold by Bayer under the trade name BAYCUSAN®, such as BAYCUSAN® C1000, BAYCUSAN® C1001, BAYCUSAN® C1003, and BAYCUSAN® C1004.

The latex polymer may utilize an acrylate latex polymer, and in particular a styrene/acrylate copolymer. Non-limiting examples of suitable styrene/acrylate copolymers include, but are not limited to, DAITOSOL® 5000 STY sold by Kobo Products, Inc.; JONCRYL® 77 sold by BASF; NEOCRYL® BT-62 sold by Neoresins, Inc.; RHOPLEX™ P-376 and UCA™ DL 432S sold by Dow Chemical Company; and YODOSOL GH41 and YODOSOL GH840 sold by AkzoNobel.

The latex polymer may utilize an acrylamide/acrylate copolymer such as acrylic acid/ethyl acrylate/t-butyl acrylamide copolymer, acrylates/octylacrylamide copolymer, and octylacrylamide/acrylates/methacrylates copolymer. Non-limiting examples of suitable acrylamide/acrylate copolymers include AMPHOMER® LV-71 and DERMACRYL® 79 sold by AkzoNobel and ULTRAHOLD® STRONG sold by BASF.

The latex polymer may be chosen from blends comprising a combination of latex film formers, including, for example, a blend of any of the above-mentioned film formers.

The latex polymer(s) should be present in the composition in a total amount of between 1 and 25% by weight.

Waxes

The composition may include at least one wax. As used herein, "wax" may be any lipophilic fatty compound. The waxes may be hydrocarbon-based waxes, fluoro waxes and/or silicone waxes and may be of plant, mineral, animal and/or synthetic origin. Non-limiting examples of suitable waxes include waxes of natural origin such as beeswax, carnauba wax, candelilla wax, ouricury wax, Japan wax, cork fiber wax, paraffin wax, microcrystalline wax, sugar cane wax, lignite wax, montan wax, hydrogenated oils, waxes of synthetic origin, and the like.

The waxes, if used, are generally present in the composition in a total amount of from about 1% to about 50% by weight. In some embodiments, the waxes are present in the composition in a total amount of at least about 10% by weight. In some embodiments, the waxes are present in the composition in a total amount of at least about 15% by weight.

Polyhydroxyalkanoates

The polyhydroxyalkanoates drive the improvements in volume and removability and are biodegradable. As is known in the art, PHAs are a sub-family of polyesters, which can be made with hydroxyl carboxylic acid monomers, which of various chain lengths. Surprisingly, not all polyhydroxyalkanoates can perform adequately in the disclosed compositions.

Here, the monomers of the polyhydroxyalkanoate should be in the form of a powder. This will preferably involve PHAs comprised of at least one monomer that has a carbon chain length of between 3 and 5. Preferred PHAs utilize short chain length monomers, and are thus based on carboxylic acids having 3 carbons (propionic or propanoic acid), 4 carbons (butyric or butanoic acid), or 5 carbons (valeric or pentanoic acid).

Non-limiting examples of these PHAs includes the following.

Polyhydroxybutyrate (PHB or PH3B). Polyhydroxybutyrate is a polymer of 3 hydroxybutyric acid, and conforms to the formula represented by the structure shown below:

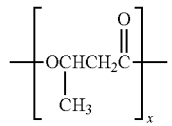

This is also known as: Butanoic acid, 3-hydroxy-, (3R)—, homopolymer, and is, available commercially as, e.g., PHB from Metabolix or TianAn Biopolymer or Eckart or Micro Powders Hydroxybutyric Acid/Hydroxypentanoic Acid Copolymer (PHB-PHV copolymer). Hydroxybutyric Acid/Hydroxypentanoic Acid Copolymer is the copolymer that conforms generally to the structure shown below.

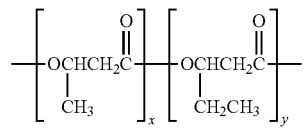

This is also known as: Pentanoic acid, 3-hydroxy-, (3R)—, polymer with (3R)-3-hydroxybutanoic acid, and has an INCI name of Hydroxybutyric Acid/Hydroxypentanoic copolymer.

Poly(3-hydroxybutyrate-co-3-hydroxyvalerate) (PHBV). Poly(3-hydroxybutyrate-co-3-hydroxyvalerate) is the copolymer of hydroxybutyric acid and hydroxypentanoic acid that conforms generally to the structure below:

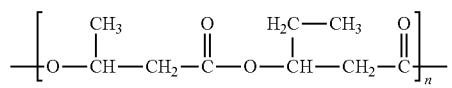

Various suitable PHAs can be obtained from Eckart (a member of the Altana group), Tianan Enmat or MicroPowders.

Other non-limiting examples of suitable polyhydroxyalkanoates include poly-3-hydroxyproprionate (P3HP), poly-3-hydroxyvalerate (PHV), and poly-4-hydroxybutyrate (P4HB). In preferred embodiments, the composition does not include any polyhydroxyalkanoates with monomers having a carbon chain length greater than 5.

In other embodiments, the PHA is comprised of at least one monomer having a carbon chain length of between 3 and 5, and one or more monomers having a carbon chain length of between 5 and 10.

In certain embodiments, the monomers in all PHAs have carbon chain lengths of between 3 and 6. For example, in certain embodiments, the PHA contains a monomer based on hexanoic acid.

In some embodiments, two or fewer polyhydroxyalkanoates are utilized, and in particular, the only polyhydroxyalkanoates that are used are PH3B, PHBV, or a combination thereof. In some embodiments, any polyhydroxyalkanoate that is present is composed of only one monomer (i.e., PH3B), while in other embodiments, all polyhydroxyalkanoates that are present are copolymers (i.e., PHBV).

Polyhydroxyalkanoates are generally provided in powder form. In some embodiments, the polyhydroxyalkanoate is present as a generally spherical particle, and in particular, a particle with an average particle size/diameter (d50) of between about 0.1 nm and about 100 μm, such as between about 0.1 nm and about 50 μm, and preferably between about 3 μm and about 50 μm.

The polyhydroxyalkanoate(s) should be present in the composition in a total amount of between about 0.5% and about 15% by weight, preferentially to 1 to about 5% by weight.

Optionally, the composition may include other ingredients, such as colorants, cellulose or cellulose derivative, surfactants, hydrophilic gelling agents, lipophilic gelling agents, cosmetic active agents, oils or organic solvents, or preservatives.

Colorants

The disclosed compositions may include one or more colorants.

Colorants are preferably chosen from pulverulent materials, liposoluble dyes and water-soluble dyes, and mixtures thereof.

Preferably, the compositions according to the invention comprise at least one pulverulent colorant. The pulverulent colorants may be chosen from pigments and nacres, and preferably from pigments.

The pigments may be white or colored, inorganic and/or organic, and coated or uncoated. Among the inorganic pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminum.

The nacres may be chosen from white nacreous pigments such as mica coated with titanium or with bismuth oxychloride, colored nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides.

These colorants may be present in a content ranging from 0.01% to 30% by weight relative to the total weight of the composition and in particular from 6% to 22% by weight relative to the total weight of the composition.

Preferably, the colorant(s) is (are) chosen from one or more metal oxides that are present in a content of greater than or equal to 2% by weight relative to the total weight of the composition, and advantageously inclusively between 6% and 22% by weight relative to the total weight of the composition.

Cellulose or Cellulose Derivative

The composition may include cellulose or a cellulose derivative.

Non-limiting examples of cellulose derivatives include sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose, and also quaternized cellulose derivatives.

Cellulose can be obtained from Daito Kasei or from Evonik, or JRS Rettenmaier.

In some embodiments, the composition is preferably free of cellulose or cellulose derivatives.

When present, the cellulose or a cellulose derivative are generally present in a total content preferably of less than 10% by weight relative to the total weight of the composition.

Surfactants

The composition may include an anionic, cationic, non-ionic and/or amphoteric surfactant.

When present, the surfactants are generally present in a total content preferably of less than 25% by weight relative to the total weight of the composition.

Hydrophilic Gelling Agents

The compositions according to the present invention may also contain at least one hydrophilic, or water-soluble, gelling agent. Such gelling agents include, but are not limited to:

acrylic or methacrylic acid homopolymers or copolymers or the salts thereof and esters thereof and in particular the products sold under the names Versicol F® or Versicol K® by the company Allied Colloid, Ultrahold 8® by the company Ciba-Geigy, and polyacrylic acids of Synthalen K type;

copolymers of acrylic acid and of acrylamide sold in the form of the sodium salt thereof under the names Reten® by the company Hercules, and the sodium salts of polyhydroxycarboxylic acids sold under the name Hydagen F® by the company Henkel, polyacrylic acid/alkyl acrylate copolymers of Pemulen type;

AMPS (polyacrylamidomethylpropanesulfonic acid partially neutralized with aqueous ammonia and highly crosslinked) sold by the company Clariant;

AMPS/acrylamide copolymers of SepiGel® or Simul-Gel® type sold by the company SEPPIC;

AMPS/polyoxyethylenated alkyl methacrylate copolymers (crosslinked or non-crosslinked), and mixtures thereof;

associative polymers and in particular associative polyurethanes such as the $C_{16}$-$OE_{120}$-$C_{16}$ polymer from the company Elementis (sold under the name RHEOLATE FX1100, this molecule bearing a urethane function and having a weight-average molecular weight of 1300), OE being an oxyethylene unit, RHEOLATE 205 bearing a urea function, sold by the company Rheox, or also RHEOLATE 208 or 204 (these polymers being sold in pure form) or DW 1206B from ROhm & Haas bearing a $C_{20}$ alkyl chain and a urethane bond, sold at 20% solids in water. It is also possible to use solutions or dispersions of these associative polyurethanes, in particular in water or in aqueous-alcoholic medium. Examples of such polymers that may be mentioned include RHEOLATE FX1010, RHEOLATE FX1035, RHEOLATE 1070, RHEOLATE 255, RHEOLATE 278 and RHEOLATE 244 sold by the company Elementis. It is also possible to use the products DW 1206F and DW 1206J, and also ACRYSOL RM 184 or ACRYSOL 44 from the company Rohm & Haas, or alternatively -BORCHIGEL LW 44 from the company Borchers;

and mixtures thereof.

Some water-soluble film-forming polymers also act as water-soluble gelling agent.

The hydrophilic gelling agents may be present in the compositions according to the invention in a content ranging from 0.05% to 10% by weight, relative to the total weight of the composition.

Lipophilic Gelling Agents

A composition may comprise at least one lipophilic or liposoluble gelling agent.

The gelling agent(s) that may be used may be organic or mineral, polymeric or molecular lipophilic gelling agents.

Mineral lipophilic gelling agents that may be mentioned include clays, modified clays, such as -BENTONE 38 VCG by the company Elementis, and optionally hydrophobically surface-treated fumed silica.

The polymeric organic lipophilic gelling agents are, for example, partially or completely crosslinked elastomeric organopolysiloxanes of three-dimensional structure, such as the products sold under the names KSG6®, KSG16® and KSG18® by the company Shin-Etsu, TREFIL E-505C® and Trefil E-5060® by the company Dow Corning, Gransil SR-CYC®, SR DMF10®, SR-DC556®, SR SCYC Gel®, SR DMF 10 Gel® and SR DC 556 Gel® by the company Grant Industries and SF 1204® and JK 113® by the company General Electric; ethyl cellulose, such as the product sold under the name Ethocel® the company by Dow Chemical; polycondensates of polyamide type resulting from the condensation between (a) at least one acid chosen from dicarboxylic acids containing at least 32 carbon atoms, such as fatty acid dimers, and (β) an alkylenediamine and in particular ethylenediamine, in which the polyamide polymer comprises at least one carboxylic acid end group esterified or amidated with at least one saturated and linear monoalcohol or monoamine containing from 12 to 30 carbon atoms, and in particular ethylenediamine/stearyl dilinoleate copolymers such as the product sold under the name Uniclear 100 VG® by the company Arizona Chemical; silicone polyamides of the polyorganosiloxane type such as those described in documents U.S. Pat. Nos. 5,874,069, 5,919, 441, 6,051,216 and 5,981,680, for instance the products sold under the references Dow Corning 2-8179 and Dow Corning 2-8178 Gellant by the company Dow Corning. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly (ethylene-propylene) type, such as the products sold under the name Kraton® by the company Shell Chemical Co., or also of the polystyrene/copoly(ethylene-butylene) type, and mixtures of triblock and radial (star) copolymers in isododecane, such as the products sold by the company Penreco under the name Versagel®, for instance the mixture of butylene/ethylene/styrene triblock copolymer and of ethylene/propylene/styrene star copolymer in isododecane (-VERSAGEL M 5960).

The compositions may also comprise a non-emulsifying silicone elastomer as lipophilic gelling agent. Among the lipophilic gelling agents that may also be mentioned are organogelling agents.

In some embodiments, the composition is preferably free of lipophilic gelling agent.

Cosmetic Active Agents

The composition may also comprise at least one cosmetic active agent.

As cosmetic active agents that may be used in the compositions in accordance with the invention, mention may be made in particular of antioxidants, preserving agents, fragrances, neutralizers, emollients, coalescers, moisturizers, vitamins and screening agents, in particular sunscreens, and mixtures thereof.

Needless to say, those skilled in the art will take care to select the optional additional ingredients and/or the amount thereof such that the advantageous properties of the composition are not, or are not substantially, adversely affected by the envisaged addition.

Oil or Organic Solvent

The compositions may comprise at least one oil or organic solvent. The compositions according to the invention may in particular comprise at least one oil chosen from at least one non-volatile oil, at least one volatile oil, and a mixture thereof.

Non-Volatile Oil

The term "oil" is intended to mean a fatty substance that is liquid at ambient temperature and at atmospheric pressure.

The term "non-volatile oil" is intended to mean an oil that remains on the skin or the keratin fibre at ambient temperature and pressure. More precisely, a non-volatile oil has an evaporation rate strictly less than 0.01 mg/cm$^2$/min. To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

Said at least one non-volatile oil may be chosen from hydrocarbon-based oils and silicone oils, and mixtures thereof, preferably from hydrocarbon-based oils.

The non-volatile hydrocarbon-based oils that are suitable for the present invention may be chosen in particular from:

hydrocarbon-based oils of plant origin, such as triglycerides consisting of fatty acid esters of glycerol, the fatty acids of which may have chain lengths ranging from C4 to C28, these fatty acids possibly being linear or branched, and saturated or unsaturated; these oils are in particular wheatgerm oil, sunflower oil, grapeseed oil, sesame oil, corn oil, apricot oil, castor oil, shea oil, avocado oil, olive oil, soybean oil, sweet almond oil, rapeseed oil, cottonseed oil, hazelnut oil, macadamia oil, jojoba oil, palm oil, alfalfa oil, poppy oil, pumpkin oil, marrow oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by the company Stearineries Dubois or those sold under the names Miglyol 810®, 812® and 818® by the company Sasol;

synthetic ethers containing from 10 to 40 carbon atoms;

linear or branched hydrocarbons of mineral or synthetic origin other than the polymers according to the invention, such as petroleum jelly, polybutenes, polydecenes and squalane, and mixtures thereof;

synthetic esters such as the oils of formula R1COOR2 in which R1 represents the linear or branched fatty acid residue containing from 1 to 40 carbon atoms and R2 represents an in particular branched hydrocarbon-based chain containing from 1 to 40 carbon atoms, on condition that R1+R2 10, for instance purcellin oil (cetostearyl octanoate), isopropyl myristate, isopropyl palmitate, C12 to C15 alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearate lactate and diisostearyl malate; and pentaerythritol esters;

fatty alcohols that are liquid at ambient temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol; and higher fatty acids such as oleic acid, linoleic acid or linolenic acid, and mixtures thereof.

Non-limiting examples of suitable non-volatile silicone oils that may be used in the composition in accordance with the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, such as phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

A composition optionally comprises at least one non-volatile hydrocarbon-based oil of plant origin, such as triglycerides consisting of fatty acid esters of glycerol the fatty acids of which may have chain lengths ranging from C4 to C28, in particular palm oil and hydrogenated jojoba oil. A composition is preferably free of silicone non-volatile oil(s).

A composition is preferably free of non-volatile oil. However, the total content of non-volatile oil(s) in a composition in accordance with the invention may range from 0.01% to 10% by weight, in particular from 0.1% to 8% by weight and preferably from 0.25% to 5% by weight relative to the total weight of the composition.

According to one preferred embodiment, a composition comprises less than 5% by weight of non-volatile oil(s) relative to the total weight of the composition.

Volatile Oil

The composition may comprise at least one volatile oil.

The term "volatile oil" is intended to mean an oil (or non-aqueous medium) that can evaporate on contact with the skin in less than one hour, at ambient temperature and atmospheric pressure. The volatile oil is a cosmetic volatile oil, which is liquid at ambient temperature. More specifically, a volatile oil has an evaporation rate of between 0.01 and 200 mg/cm$^2$/min, limits included.

This volatile oil may be hydrocarbon-based.

The volatile hydrocarbon-based oil may be chosen from hydrocarbon-based oils containing from 7 to 16 carbon atoms.

The composition may contain one or more volatile branched alkanes. The expression "one or more volatile branched alkanes" is intended to mean, without preference, "one or more volatile branched alkane oils".

As a volatile hydrocarbon-based oil containing from 7 to 16 carbon atoms, mention may be made in particular of C8-C16 branched alkanes, such as C8-C16 isoalkanes (also known as isoparaffins), isododecane, isodecane, isohexadecane and for example the oils sold under the trade names Isopar or Permethyl, C8-C16 branched esters such as isohexyl neopentanoate, and mixtures thereof. Preferably, the volatile hydrocarbon-based oil containing from 8 to 16 carbon atoms is chosen from isododecane, isodecane and isohexadecane, and mixtures thereof, and is in particular isododecane.

The composition may contain one or more volatile linear alkanes. The term "one or more volatile linear alkanes" is intended to mean, without preference, "one or more volatile linear alkane oils".

A volatile linear alkane that is suitable for the invention is liquid at ambient temperature (about 25° C.) and at atmospheric pressure (760 mmHg).

A "volatile linear alkane" that is suitable for the invention is intended to mean a cosmetic linear alkane, which is capable of evaporating on contact with the skin in less than one hour, at ambient temperature (25° C.) and atmospheric pressure (760 mmHg), which is liquid at ambient temperature, in particular having an evaporation rate ranging from 0.01 to 15 mg/cm$^2$/min, at ambient temperature (25° C.) and atmospheric pressure (760 mmHg).

The linear alkanes, preferably of plant origin, comprise from 7 to 15 carbon atoms, in particular from 9 to 14 carbon atoms and more particularly from 11 to 13 carbon atoms.

Non limiting examples of suitable alkanes are described in patent applications WO 2007/068,371 or WO 2008/155, 059 by the company Cognis (mixtures of distinct alkanes that differ by at least one carbon). These alkanes are obtained from fatty alcohols, which are themselves obtained from coconut oil or palm oil.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155 059 by the company Cognis. Mention may also be made of n-dodecane (C12) and n-tetradecane (C14) sold by Sasol under the references, respectively, Parafol 12-97 and Parafol 14-97, and also mixtures thereof.

The linear alkane may be used alone or as a mixture of at least two distinct alkanes that differ from each other by a carbon number of at least 1, and in particular a mixture of at least two linear alkanes comprising from 10 to 14 distinct carbon atoms that differ from each other by a carbon number of at least 2, and in particular a mixture of C11/C13 volatile linear alkanes or a mixture of C12/C14 linear alkanes, in particular an n-undecane/n-tridecane mixture.

As a variant or additionally, the composition prepared may comprise at least one volatile silicone oil or solvent that is compatible with cosmetic use.

The term "silicone oil" is intended to mean an oil containing at least one silicon atom, and in particular containing Si—O groups. According to one embodiment, said composition comprises less than 10% by weight of non-volatile silicone oil(s), relative to the total weight of the composition, better still less than 5% by weight, or even is free of silicone oil.

Volatile silicone oils that may be mentioned include cyclic polysiloxanes and linear polysiloxanes, and mixtures thereof. Volatile linear polysiloxanes that may be mentioned include hexamethyldisiloxane, octamethyltrisiloxane, decamethyltetrasiloxane, tetradecamethylhexasiloxane and hexadecamethylheptasiloxane. Volatile cyclic polysiloxanes that may be mentioned include hexamethylcyclotrisiloxane, octamethylcyclotetrasiloxane, decamethylcyclopentasiloxane and dodecamethylcyclohexasiloxane.

A composition is preferably free of non-volatile oil.

In some embodiments, at least one volatile oil, and preferably a volatile hydrocarbon-based oil, may be present in a total amount of at least about 30% by weight, such as between about 30% to about 60% by weight.

According to one embodiment, a composition comprises less than 5% by weight of volatile oil(s) relative to the total weight of the composition.

Also disclosed is a method for treating eyelashes. The method includes applying previously disclosed cosmetic composition to an eyelash and allowing the cosmetic composition to remain in contact with the eyelash. The cosmetic composition may remain on the eyelash for between 5 minutes and 24 hours, after which time it may optionally be removed using standard makeup-removal techniques.

EXAMPLES

An embodiment of a disclosed composition can be seen in Table 1, below.

TABLE 1

| Material | % w/w |
| --- | --- |
| Waterproofing Agent(s) (Waxes and/or Latex Polymer) | 10-25% |
| PH3B | 1-5% |
| Volatile Solvent | 5-50% |
| Surfactant System | 5-15% |
| Pigments (Iron Oxides) | 5-15% |
| Preservatives | <2% |

The compositions were prepared as follows. The ingredients were weighed out, and the volatile solvents, and waterproofing agent(s) were combined, then heated to 70° C. and mixed. The PH3B, surfactant system, and pigments were then added and mixed. After cooling to below 40° C., the preservatives were added. The composition thus obtained was transferred into a closed jar to prevent it from drying out on contact with air; then allowed to sit for 24 hours before checking the homogeneity of the formulation and the correct dispersion of the pigments.

Evaluations

A base formulation with no PHA/filler agent (comparative formula 1) was compared with the base formula with 3% cellulose (comparative formula 2) and the base formula with 3% of 10 μm PH3B (exemplary formula 1) and 3% of 10 μm PHBV (exemplary formula 2).

30 strokes of each mascara were applied onto fake lashes and left to dry overnight.

Volume. Comparative formula 2 and the exemplary formulas ere compared to comparative formula 1, and the increase in volume of the lashes was visually assessed. Both the comparative formula 2 and the exemplary formula provided a visual increase in volume of approximately 50% over exemplary formula 1. Exemplary formula 2 provided a visual increase in volume over exemplary formula 1, but less of an increase than exemplary formula 1.

Removal. The lashes were soaked in water for 1 hour. Using a round cotton pad soaked with water, each lash was squeezed for 30 times. Afterwards, each lash was rated on a scale of 1-3 on the residual remaining on the lash. The exemplary formulas each had a removal rating of "3", while comparative formula 1 had a rating of "1", and comparative formula 2 had a rating of "2".

Those skilled in the art will recognize or be able to ascertain using no more than routine experimentation, many equivalents to the specific embodiments of the invention described herein. Such equivalents are intended to be encompassed by the following claims.

What is claimed is:

1. A cosmetic composition comprising:
   at least one waterproofing agent, the at least one waterproofing agent consisting of a latex polymer; and
   at least one polyhydroxyalkanoate,
   wherein the at least one polyhydroxyalkanoate is present in the composition in a total amount of between about 1% and about 5% by weight,
   wherein each of the at least one polyhydroxyalkanoates is composed of at least one monomer having a carbon chain length of L, where $3 \leq L \leq 5$, and
   wherein the composition contains water, the water being present in a total amount of less than about 10% by weight.

2. The cosmetic composition according to claim 1, wherein the at least one polyhydroxyalkanoate is poly-3-hydroxybutyrate (PH3B), poly(3-hydroxybutyrate-co-3-hydroxyvalerate) (PHBV), or a combination thereof.

3. The cosmetic composition according to claim 1, wherein each of the at least one polyhydroxyalkanoates is composed of one monomer.

4. The cosmetic composition according to claim 1, further comprising a colorant.

5. The cosmetic composition according to claim 1, further comprising at least one wax.

6. The cosmetic composition according to claim 1, wherein the polyhydroxyalkanoate is a solid particle in powder form.

7. The cosmetic composition according to claim 6, wherein the average particle size (d50) of the polyhydroxyalkanoate is between about 0.1 nm and 100 μm.

8. The cosmetic composition according to claim 1, wherein the composition does not include any polyhydroxyalkanoates with monomers having a carbon chain length greater than 5.

9. The cosmetic composition according to claim 1, wherein the composition does not include any cellulose or cellulose derivatives.

10. The cosmetic composition according to claim 1, further comprising a preservative.

11. The cosmetic composition according to claim 1, further comprising a surfactant.

12. The cosmetic composition according to claim 1, further comprising a hydrophilic gelling agent.

13. The cosmetic composition according to claim 1, further comprising a lipophilic gelling agent.

14. A method for treating eyelashes, comprising the steps of:
   applying a cosmetic composition according to claim 1 to an eyelash; and
   allowing the cosmetic composition to remain in contact with the eyelash.

15. The method according to claim 14, further comprising allowing the cosmetic composition to remain on the eyelash for between 5 minutes and 24 hours.

16. The method according to claim 14, further comprising removing the cosmetic composition.

17. A cosmetic composition comprising:
   at least one waterproofing agent, the at least one waterproofing agent consisting of a latex polymer; and
   at least one polyhydroxyalkanoate,
   wherein the at least one polyhydroxyalkanoate is present in the composition in a total amount of between about 1% and about 5% by weight,
   wherein each of the at least one polyhydroxyalkanoates is a powder, and
   wherein the composition contains water, the water being present in a total amount of less than about 10% by weight.

* * * * *